United States Patent
Rothe et al.

(10) Patent No.: US 6,855,815 B2
(45) Date of Patent: Feb. 15, 2005

(54) INHIBITORS OF APOPTOSIS

(75) Inventors: Mike Rothe, San Mateo, CA (US); David V. Goeddel, Hillsborough, CA (US)

(73) Assignee: Amgen Inc., South San Francisco, CA (US)

( * ) Notice: Subject to any disclaimer, the term of this patent is extended or adjusted under 35 U.S.C. 154(b) by 147 days.

(21) Appl. No.: 10/232,286

(22) Filed: Aug. 30, 2002

(65) Prior Publication Data

US 2003/0143579 A1 Jul. 31, 2003

Related U.S. Application Data

(62) Division of application No. 09/689,366, filed on Oct. 12, 2000, now Pat. No. 6,821,736, which is a division of application No. 08/569,749, filed on Dec. 8, 1995, now Pat. No. 6,187,557, which is a continuation of application No. 08/512,946, filed on Aug. 8, 1995, now abandoned.

(51) Int. Cl.[7] .................. C07H 21/04; A01N 43/04; G01N 3/53; C12N 15/00; C12N 15/09
(52) U.S. Cl. ................ 536/24.5; 514/44; 435/7; 435/320.1
(58) Field of Search ............... 536/24.5; 514/44; 435/7, 320.1

(56) References Cited

U.S. PATENT DOCUMENTS

| | | |
|---|---|---|
| 5,919,912 A | 7/1999 | Korneluk et al. |
| 5,958,771 A | 9/1999 | Bennett et al. |
| 5,958,772 A | 9/1999 | Bennett et al. |

OTHER PUBLICATIONS

Anderson Human Gene TherapyNature vol. 392, supp 1998 pp25–30.*
Verma et al. Gene Therapy Promises Problems and Prospects Nature vol. 389 1997 pp239–242.*
Palu et al. In pursuit of new developments for gene therapy of human diseases J. of Biotech. vol. 68 1999 pp1–12.*
Branch A good antisense in hard to find. TIBS 23:45–50 1998 pp45–50.*
Tamm et al. Antisense therapy in oncology: a new hope for an old idea? The Lancet vol. 358 2001 pp489–496.*
Jen et al. Suppression of Gene Expression by Targeted Disruption of mRNA: Available Options and Current Strategies Stem Cells vol. 18 2000 pp307–319.*
Marshall, E (1995) Science 269:1050–1055.
Vile et al. (1995) Targeted Gene Therapy 9: 190–199.
Birnbaum et al. (1994) J. Virol. 68: 2521–2528.
M. Rothe et al. (1995) Cell 83: 1243–1252.
A Fernandez et al. (1994) Cancer Bulletin 46: 153–160.
DL Vaux et al. (1996) Proc. Natl. Acad. Sci. USA 93: 2239–2244.
L Hillier et al. (Apr. 5, 1995) EST accession No. R07927. Accessed Feb. 21, 1997.
L Hillier et al. (Mar. 27, 1995) EST accession No. T96284. Accessed Feb. 21, 1997.

* cited by examiner

*Primary Examiner*—James Ketter
*Assistant Examiner*—Konstantina Katcheves
(74) *Attorney, Agent, or Firm*—Richard Aron Osman

(57) ABSTRACT

The invention provides methods and compositions relating to novel human cellular inhibitor of apoptosis proteins (c-IAP1/2) comprising a series of defined structural domain repeats and/or a RING finger domain; in particular, at least two of: a particular first domain repeat, a particular second domain repeat, and a particular third domain repeat, and/or a particular RING finger domain. The proteins provide a c-IAP specific function, with preferred proteins being capable of modulating the induction of apoptosis; for example, by binding a human tumor necrosis factor receptor associated factor (TRAF). The compositions include nucleic acids which encode the subject c-IAP and hybridization probes and primers capable of hybridizing with the disclosed c-IAP genes. The invention includes methods of using the subject compositions in therapy, in diagnosis and in the biopharmaceutical industry.

5 Claims, No Drawings

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 2589 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

```
TCTAAGTAGT ATCTTGGAAA TTCAGAGAGA TACTCATCCT ACCTGAATAT AAACTGAGAT      60

AAATCCAGTA AAGAAAGTGT AGTAAATTCT ACATAAGAGT CTATCATTGA TTTCTTTTGG     120

TGGTAAAAAT CTTAGTTCAT GTGAAGAAAT TTCATGTGAA TGTTTTAGCT ATCAAACAGC     180

ACTGTCACCT ACTCATGCAC AAAACTGCCT CCCAAAGACT TTTCCCAGGT CCCTCGTATC     240

AAAACATTAA GAGTATAATG AAGATAGCA CGATCTTGTC AGATTGGACA AACAGCAACA      300

AACAAAAAAT GAAGTATGAC TTTTCCTGTG AACTCTACAG AATGTCTACA TATTCAACTT     360

TCCCCGCCGG GGTGCCTGTC TCAGAAAGGA GTCTTGCTCG TGCTGGTTTT TATTATACTG     420

GTGTGAATGA CAAGGTCAAA TGCTTCTGTT GTGGCCTGAT GCTGGATAAC TGGAAACTAG     480

GAGACAGTCC TATTCAAAAG CATAAACAGC TATATCCTAG CTGTAGCTTT ATTCAGAATC     540

TGGTTTCAGC TAGTCTGGGA TCCACCTCTA AGAATACGTC TCCAATGAGA AACAGTTTTG     600

CACATTCATT ATCTCCCACC TTGGAACATA GTAGCTTGTT CAGTGGTTCT TACTCCAGCC     660

TTTCTCCAAA CCCTCTTAAT TCTAGAGCAG TTGAAGACAT CTCTTCATCG AGGACTAACC     720

CCTACAGTTA TGCAATGAGT ACTGAAGAAG CCAGATTTCT TACCTACCAT ATGTGGCCAT     780

TAACTTTTTT GTCACCATCA GAATTGGCAA GAGCTGGTTT TTATTATATA GGACCTGGAG     840

ATAGGGTAGC CTGCTTTGCC TGTGGTGGGA AGCTCAGTAA CTGGGAACCA AAGGATGATG     900

CTATGTCAGA ACACCGGAGG CATTTTCCCA ACTGTCCATT TTTGGAAAAT TCTCTAGAAA     960

CTCTGAGGTT TAGCATTTCA AATCTGAGCA TGCAGACACA TGCAGCTCGA ATGAGAACAT    1020

TTATGTACTG GCCATCTAGT GTTCCAGTTC AGCCTGAGCA GCTTGCAAGT GCTGGTTTTT    1080

ATTATGTGGG TCGCAATGAT GATGTCAAAT GCTTTTGTTG TGATGGTGGC TTGAGGTGTT    1140

GGGAATCTGG AGATGATCCA TGGGTAGAAC ATGCCAAGTG GTTTCCAAGG TGTGAGTTCT    1200

TGATACGAAT GAAAGGCCAA GAGTTTGTTG ATGAGATTCA AGGTAGATAT CCTCATCTTC    1260

TTGAACAGCT GTTGTCAACT TCAGATACCA CTGGAGAAGA AAATGCTGAC CCACCAATTA    1320

TTCATTTTGG ACCTGGAGAA AGTTCTTCAG AAGATGCTGT CATGATGAAT ACACCTGTGG    1380

TTAAATCTGC CTTGGAAATG GCTTTAATA GAGACCTGGT GAAACAAACA GTTCAAAGTA     1440

AAATCCTGAC AACTGGAGAG AACTATAAAA CAGTTAATGA TATTGTGTCA GCACTTCTAA    1500

ATGCTGAAGA TGAAAAAAGA GAGGAGGAGA AGGAAAAACA AGCTGAAGAA ATGGCATCAG    1560

ATGATTTGTC ATTAATTCGG AAGAACAGAA TGGCTCTCTT TCAACAATTG ACATGTGTGC    1620

TTCCTATCCT GGATAATCTT TTAAAGGCCA ATGTAATTAA TAAACAGGAA CATGATATTA    1680

TTAAACAAAA AACACAGATA CCTTTACAAG CGAGAGAACT GATTGATACC ATTTTGGTTA    1740

AAGGAAATGC TGCGGCCAAC ATCTTCAAAA ACTGTCTAAA AGAAATTGAC TCTACATTGT    1800

ATAAGAACTT ATTTGTGGAT AAGAATATGA AGTATATTCC AACAGAAGAT GTTTCAGGTC    1860

TGTCACTGGA AGAACAATTG AGGAGGTTGC AAGAAGAACG AACTTGTAAA GTGTGTATGG    1920

ACAAAGAAGT TTCTGTTGTA TTTATTCCTT GTGGTCATCT GGTAGTATGC CAGGAATGTG    1980

CCCCTTCTCT AAGAAAATGC CCTATTTGCA GGGGTATAAT CAAGGGTACT GTTCGTACAT    2040

TTCTCTCTTA AAGAAAAATA GTCTATATTT TAACCTGCAT AAAAAGGTCT TTAAAATATT    2100

GTTGAACACT TGAAGCCATC TAAAGTAAAA AGGGAATTAT GAGTTTTTCA ATTAGTAACA    2160

TTCATGTTCT AGTCTGCTTT GGTACTAATA ATCTTGTTTC TGAAAAGATG GTATCATATA    2220

TTTAATCTTA ATCTGTTTAT TTACAAGGGA AGATTTATGT TTGGTGAACT ATATTAGTAT    2280

GTATGTGTAC CTAAGGGAGT AGTGTCACTG CTTGTTATGC ATCATTTCAG GAGTTACTGG    2340
```

```
ATTTGTTGTT CTTTCAGAAA GCTTTGAATA CTAAATTATA GTGTAGAAAA GAACTGGAAA    2400

CCAGGAACTC TGGAGTTCAT CAGAGTTATG GTGCCGAATT GTCTTTGGTG CTTTTCACTT    2460

GTGTTTTAAA ATAAGGATTT TTCTCTTATT TCTCCCCCTA GTTTGTGAGA AACATCTCAA    2520

TAAAGTGCTT TAAAAAAAAA AAAAAAAAAA AAAAAAAAAA AAAAAAAAAA AAAAAAAAAA    2580

AAAAAAAAA                                                           2589
```

(2) INFORMATION FOR SEQ ID NO: 2:

(i) SEQUENCE CHARACTERISTICS:
        (A) LENGTH: 618 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Met His Lys Thr Ala Ser Gln Arg Leu Phe Pro Gly Pro Ser Tyr Gln
 1               5                  10                  15

Asn Ile Lys Ser Ile Met Glu Asp Ser Thr Ile Leu Ser Asp Trp Thr
                20                  25                  30

Asn Ser Asn Lys Gln Lys Met Lys Tyr Asp Phe Ser Cys Glu Leu Tyr
            35                  40                  45

Arg Met Ser Thr Tyr Ser Thr Phe Pro Ala Gly Val Pro Val Ser Glu
        50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Leu Gly
                85                  90                  95

Asp Ser Pro Ile Gln Lys His Lys Gln Leu Tyr Pro Ser Cys Ser Phe
                100                 105                 110

Ile Gln Asn Leu Val Ser Ala Ser Leu Gly Ser Thr Ser Lys Asn Thr
            115                 120                 125

Ser Pro Met Arg Asn Ser Phe Ala His Ser Leu Ser Pro Thr Leu Glu
        130                 135                 140

His Ser Ser Leu Phe Ser Gly Ser Tyr Ser Ser Leu Ser Pro Asn Pro
145                 150                 155                 160

Leu Asn Ser Arg Ala Val Glu Asp Ile Ser Ser Ser Arg Thr Asn Pro
                165                 170                 175

Tyr Ser Tyr Ala Met Ser Thr Glu Glu Ala Arg Phe Leu Thr Tyr His
            180                 185                 190

Met Trp Pro Leu Thr Phe Leu Ser Pro Ser Glu Leu Ala Arg Ala Gly
        195                 200                 205

Phe Tyr Tyr Ile Gly Pro Gly Asp Arg Val Ala Cys Phe Ala Cys Gly
    210                 215                 220

Gly Lys Leu Ser Asn Trp Glu Pro Lys Asp Asp Ala Met Ser Glu His
225                 230                 235                 240

Arg Arg His Phe Pro Asn Cys Pro Phe Leu Glu Asn Ser Leu Glu Thr
                245                 250                 255

Leu Arg Phe Ser Ile Ser Asn Leu Ser Met Gln Thr His Ala Ala Arg
            260                 265                 270

Met Arg Thr Phe Met Tyr Trp Pro Ser Ser Val Pro Val Gln Pro Glu
        275                 280                 285

Gln Leu Ala Ser Ala Gly Phe Tyr Tyr Val Gly Arg Asn Asp Asp Val
```

```
                    290                 295                 300
Lys Cys Phe Cys Cys Asp Gly Gly Leu Arg Cys Trp Glu Ser Gly Asp
305                 310                 315                 320

Asp Pro Trp Val Glu His Ala Lys Trp Phe Pro Arg Cys Glu Phe Leu
                325                 330                 335

Ile Arg Met Lys Gly Gln Glu Phe Val Asp Glu Ile Gln Gly Arg Tyr
            340                 345                 350

Pro His Leu Leu Glu Gln Leu Leu Ser Thr Ser Asp Thr Thr Gly Glu
                355                 360                 365

Glu Asn Ala Asp Pro Pro Ile Ile His Phe Gly Pro Gly Glu Ser Ser
370                 375                 380

Ser Glu Asp Ala Val Met Met Asn Thr Pro Val Val Lys Ser Ala Leu
385                 390                 395                 400

Glu Met Gly Phe Asn Arg Asp Leu Val Lys Gln Thr Val Gln Ser Lys
                405                 410                 415

Ile Leu Thr Thr Gly Glu Asn Tyr Lys Thr Val Asn Asp Ile Val Ser
            420                 425                 430

Ala Leu Leu Asn Ala Glu Asp Glu Lys Arg Glu Glu Lys Glu Lys
                435                 440                 445

Gln Ala Glu Glu Met Ala Ser Asp Asp Leu Ser Leu Ile Arg Lys Asn
450                 455                 460

Arg Met Ala Leu Phe Gln Gln Leu Thr Cys Val Leu Pro Ile Leu Asp
465                 470                 475                 480

Asn Leu Leu Lys Ala Asn Val Ile Asn Lys Gln Glu His Asp Ile Ile
                485                 490                 495

Lys Gln Lys Thr Gln Ile Pro Leu Gln Ala Arg Glu Leu Ile Asp Thr
            500                 505                 510

Ile Leu Val Lys Gly Asn Ala Ala Asn Ile Phe Lys Asn Cys Leu
            515                 520                 525

Lys Glu Ile Asp Ser Thr Leu Tyr Lys Asn Leu Phe Val Asp Lys Asn
            530                 535                 540

Met Lys Tyr Ile Pro Thr Glu Asp Val Ser Gly Leu Ser Leu Glu Glu
545                 550                 555                 560

Gln Leu Arg Arg Leu Gln Glu Glu Arg Thr Cys Lys Val Cys Met Asp
                565                 570                 575

Lys Glu Val Ser Val Val Phe Ile Pro Cys Gly His Leu Val Val Cys
                580                 585                 590

Gln Glu Cys Ala Pro Ser Leu Arg Lys Cys Pro Ile Cys Arg Gly Ile
            595                 600                 605

Ile Lys Gly Thr Val Arg Thr Phe Leu Ser
610                 615

(2) INFORMATION FOR SEQ ID NO: 3:

(i) SEQUENCE CHARACTERISTICS:
        (A) LENGTH: 2601 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

GGGCAGCAGG TTTACAAAGG AGGAAAACGA CTTCTTCTAG ATTTTTTTTT CAGTTTCTTC      60

TATAAATCAA AACTACCTCC CTAGAGAAAG GCTAGTCCCT TTTCTTCCCC ATTCATTTCA     120
```

-continued

| | |
|---|---|
| TTATGAACAT AGTAGAAAAC AGCATATTCT TATCAAATTT GATGAAAAGC GCCAACACGT | 180 |
| TTGAACTGAA ATACGACTTG TCATGTGAAC TGTACCGAAT GTCTACGTAT TCCACTTTTC | 240 |
| CTGCTGGGGT CCCTGTCTCA GAAAGGAGTC TTGCTCGCGC TGGTTTCTAT TACACTGGTG | 300 |
| TGAATGACAA GGTCAAATGC TTCTGTTGTG GCCTGATGCT GGATAACTGG AAAAGAGGAG | 360 |
| ACAGTCCTAC TGAAAAGCAT AAAAAGTTGT ATCCTAGCTG CAGATTCGTT CAGAGTCTAA | 420 |
| ATTCCGTTAA CAACTTGGAA GCTACCTCTC AGCCTACTTT TCCTTCTTCA GTAACAAATT | 480 |
| CCACACACTC ATTACTTCCG GGTACAGAAA ACAGTGGATA TTTCCGTGGC TCTTATTCAA | 540 |
| ACTCTCCATC AAATCCTGTA AACTCCAGAG CAAATCAAGA TTTTTCTGCC TTGATGAGAA | 600 |
| GTTCCTACCA CTGTGCAATG AATAACGAAA ATGCCAGATT ACTTACTTTT CAGACATGGC | 660 |
| CATTGACTTT TCTGTCGCCA ACAGATCTGG CAAAAGCAGG CTTTTACTAC ATAGGACCTG | 720 |
| GAGACAGAGT GGCTTGCTTT GCCTGTGGTG GAAAATTGAG CAATTGGGAA CCGAAGGATA | 780 |
| ATGCTATGTC AGAACACCTG AGACATTTTC CCAAATGCCC ATTTATAGAA AATCAGCTTC | 840 |
| AAGACACTTC AAGATACACA GTTTCTAATC TGAGCATGCA GACACATGCA GCCCGCTTTA | 900 |
| AAACATTCTT TAACTGGCCC TCTAGTGTTC TAGTTAATCC TGAGCAGCTT GCAAGTGCGG | 960 |
| GTTTTTATTA TGTGGGTAAC AGTGATGATG TCAAATGCTT TTGCTGTGAT GGTGGACTCA | 1020 |
| GGTGTTGGGA ATCGGAGAT GATCCATGGG TTCAACATGC CAAGTGGTTT CCAAGGTGTG | 1080 |
| AGTACTTGAT AAGAATTAAA GGACAGGAGT TCATCCGTCA AGTTCAAGCC AGTTACCCTC | 1140 |
| ATCTACTTGA ACAGCTGCTA TCCACATCAG ACAGCCCAGG AGATGAAAAT GCAGAGTCAT | 1200 |
| CAATTATCCA TTTTGAACCT GGAGAAGACC ATTCAGAAGA TGCAATCATG ATGAATACTC | 1260 |
| CTGTGATTAA TGCTGCCGTG GAAATGGGCT TTAGTAGAAG CCTGGTAAAA CAGACAGTTC | 1320 |
| AGAGAAAAAT CCTAGCAACT GGAGAGAATT ATAGACTAGT CAATGATCTT GTGTTAGACT | 1380 |
| TACTCAATGC AGAAGATGAA ATAAGGGAAG AGGAGAGAGA AAGAGCAACT GAGGAAAAAG | 1440 |
| AATCAAATGA TTTATTATTA ATCCGGAAGA ATAGAATGGC ACTTTTTCAA CATTTGACTT | 1500 |
| GTGTAATTCC AATCCTGGAT AGTCTACTAA CTGCCGGAAT TATTAATGAA CAAGAACATG | 1560 |
| ATGTTATTAA ACAGAAGACA CAGACGTCTT TACAAGCAAG AGAACTGATT GATACGATTT | 1620 |
| TAGTAAAAGG AAATATTGCA GCCACTGTAT TCAGAAACTC TCTGCAAGAA GCTGAAGCTG | 1680 |
| TGTTATATGA GCATTTATTT GTGCAACAGG ACATAAAATA TATTCCCACA GAAGATGTTT | 1740 |
| CAGATCTACC AGTGGAAGAA CAATTGCGGA GACTACAAGA AGAAAGAACA TGTAAAGTGT | 1800 |
| GTATGGACAA AGAAGTGTCC ATAGTGTTTA TTCCTTGTGG TCATCTAGTA GTATGCAAAG | 1860 |
| ATTGTGCTCC TTCTTTAAGA AAGTGTCCTA TTTGTAGGAG TACAATCAAG GGTACAGTTC | 1920 |
| GTACATTTCT TTCATGAAGA AGAACCAAAA CATCATCTAA ACTTTAGAAT TAATTTATTA | 1980 |
| AATGTATTAT AACTTAACT TTCATCCTAA TTTGGTTTCC TTAAAATTTT TATTTATTTA | 2040 |
| CAACTCAACA AACATTGTTT TGTGTAACAT ATTTAATATA TGTATCTAAA CCATATGAAC | 2100 |
| ATATATTTTT TAGAAACTAA GAGAATGATA GGCTTTTGTT CTTATGAACG AAAAAGAGGT | 2160 |
| AGCACTACAA ACACAATATT CAATCAAAAT TTCAGCATTA TTGAAATTGT AAGTGAAGTA | 2220 |
| AAACTTAAGA TATTTGAGTT AACCTTTAAG AATTTTAAAT ATTTTGGCAT TGTACTAATA | 2280 |
| CCGGGAACAT GAAGCCAGGT GTGGTGGTAT GTGCCTGTAG TCCCAGGCTG AGGCAAGAGA | 2340 |
| ATTACTTGAG CCCAGGAGTT TGAATCCATC CTGGGCAGCA TACTGAGACC CTGCCTTTAA | 2400 |
| AAACAAACAG AACAAAACA AAACACCAGG GACACATTTC TCTGTCTTTT TTGATCAGTG | 2460 |
| TCCTATACAT CGAAGGTGTG CATATATGTT GAATGACATT TTAGGGACAT GGTGTTTTTA | 2520 |

```
TAAAGAATTC TGTGAGAAAA AATTTAATAA AACCCCCCAA ATTAAAAAAA AAAAAAAAA      2580

AAAAAAAAAA AAAAAAAAAA A                                               2601
```

(2) INFORMATION FOR SEQ ID NO: 4:

(i) SEQUENCE CHARACTERISTICS:
        (A) LENGTH: 604 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met Asn Ile Val Glu Asn Ser Ile Phe Leu Ser Asn Leu Met Lys Ser
1               5                   10                  15

Ala Asn Thr Phe Glu Leu Lys Tyr Asp Leu Ser Cys Glu Leu Tyr Arg
            20                  25                  30

Met Ser Thr Tyr Ser Thr Phe Pro Ala Gly Val Pro Val Ser Glu Arg
        35                  40                  45

Ser Leu Ala Arg Ala Gly Phe Tyr Tyr Thr Gly Val Asn Asp Lys Val
50                  55                  60

Lys Cys Phe Cys Cys Gly Leu Met Leu Asp Asn Trp Lys Arg Gly Asp
65                  70                  75                  80

Ser Pro Thr Glu Lys His Lys Lys Leu Tyr Pro Ser Cys Arg Phe Val
                85                  90                  95

Gln Ser Leu Asn Ser Val Asn Asn Leu Glu Ala Thr Ser Gln Pro Thr
            100                 105                 110

Phe Pro Ser Ser Val Thr Asn Ser Thr His Ser Leu Leu Pro Gly Thr
        115                 120                 125

Glu Asn Ser Gly Tyr Phe Arg Gly Ser Tyr Ser Asn Ser Pro Ser Asn
130                 135                 140

Pro Val Asn Ser Arg Ala Asn Gln Asp Phe Ser Ala Leu Met Arg Ser
145                 150                 155                 160

Ser Tyr His Cys Ala Met Asn Asn Glu Asn Ala Arg Leu Leu Thr Phe
                165                 170                 175

Gln Thr Trp Pro Leu Thr Phe Leu Ser Pro Thr Asp Leu Ala Lys Ala
            180                 185                 190

Gly Phe Tyr Tyr Ile Gly Pro Gly Asp Arg Val Ala Cys Phe Ala Cys
        195                 200                 205

Gly Gly Lys Leu Ser Asn Trp Glu Pro Lys Asp Asn Ala Met Ser Glu
210                 215                 220

His Leu Arg His Phe Pro Lys Cys Pro Phe Ile Glu Asn Gln Leu Gln
225                 230                 235                 240

Asp Thr Ser Arg Tyr Thr Val Ser Asn Leu Ser Met Gln Thr His Ala
                245                 250                 255

Ala Arg Phe Lys Thr Phe Phe Asn Trp Pro Ser Ser Val Leu Val Asn
            260                 265                 270

Pro Glu Gln Leu Ala Ser Ala Gly Phe Tyr Tyr Val Gly Asn Ser Asp
        275                 280                 285

Asp Val Lys Cys Phe Cys Cys Asp Gly Gly Leu Arg Cys Trp Glu Ser
290                 295                 300

Gly Asp Asp Pro Trp Val Gln His Ala Lys Trp Phe Pro Arg Cys Glu
305                 310                 315                 320

Tyr Leu Ile Arg Ile Lys Gly Gln Glu Phe Ile Arg Gln Val Gln Ala
```

```
                        325                 330                 335
Ser Tyr Pro His Leu Glu Gln Leu Leu Ser Thr Ser Asp Ser Pro
            340                 345                 350
Gly Asp Glu Asn Ala Glu Ser Ser Ile Ile His Phe Glu Pro Gly Glu
            355                 360                 365
Asp His Ser Glu Asp Ala Ile Met Met Asn Thr Pro Val Ile Asn Ala
    370                 375                 380
Ala Val Glu Met Gly Phe Ser Arg Ser Leu Val Lys Gln Thr Val Gln
385                 390                 395                 400
Arg Lys Ile Leu Ala Thr Gly Glu Asn Tyr Arg Leu Val Asn Asp Leu
                405                 410                 415
Val Leu Asp Leu Leu Asn Ala Glu Asp Glu Ile Arg Glu Glu Glu Arg
            420                 425                 430
Glu Arg Ala Thr Glu Glu Lys Glu Ser Asn Asp Leu Leu Ile Arg
            435                 440                 445
Lys Asn Arg Met Ala Leu Phe Gln His Leu Thr Cys Val Ile Pro Ile
    450                 455                 460
Leu Asp Ser Leu Leu Thr Ala Gly Ile Ile Asn Glu Gln Glu His Asp
465                 470                 475                 480
Val Ile Lys Gln Lys Thr Gln Thr Ser Leu Gln Ala Arg Glu Leu Ile
                485                 490                 495
Asp Thr Ile Leu Val Lys Gly Asn Ile Ala Ala Thr Val Phe Arg Asn
            500                 505                 510
Ser Leu Gln Glu Ala Glu Ala Val Leu Tyr Glu His Leu Phe Val Gln
            515                 520                 525
Gln Asp Ile Lys Tyr Ile Pro Thr Glu Asp Val Ser Asp Leu Pro Val
    530                 535                 540
Glu Glu Gln Leu Arg Arg Leu Gln Glu Glu Arg Thr Cys Lys Val Cys
545                 550                 555                 560
Met Asp Lys Glu Val Ser Ile Val Phe Ile Pro Cys Gly His Leu Val
                565                 570                 575
Val Cys Lys Asp Cys Ala Pro Ser Leu Arg Lys Cys Pro Ile Cys Arg
            580                 585                 590
Ser Thr Ile Lys Gly Thr Val Arg Thr Phe Leu Ser
        595                 600
```

(2) INFORMATION FOR SEQ ID NO: 5:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Cys Glu Leu Tyr Arg Met Ser Thr Tyr Ser Thr Phe Pro Ala Gly Val
1               5                   10                  15
Pro Val Ser Glu Arg Ser Leu Ala Arg Ala Gly Phe Tyr Tyr Thr Gly
            20                  25                  30
Val Asn Asp Lys Val Lys Cys Phe Cys Cys Gly Leu Met Leu Asp Asn
        35                  40                  45
Trp Lys Leu Gly Asp Ser Pro
    50                  55
```

-continued (2) INFORMATION FOR SEQ ID NO: 6:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Cys Glu Leu Tyr Arg Met Ser Thr Tyr Ser Thr Phe Pro Ala Gly Val
1               5                   10                  15

Pro Val Ser Glu Arg Ser Leu Ala Arg Ala Gly Phe Tyr Tyr Thr Gly
                20                  25                  30

Val Asn Asp Lys Val Lys Cys Phe Cys Cys Gly Leu Met Leu Asp Asn
            35                  40                  45

Trp Lys Arg Gly Asp Ser Pro
    50                  55
```

(2) INFORMATION FOR SEQ ID NO: 7:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Leu Ala Arg Ala Gly Phe Tyr Tyr Ile Gly Pro Gly Asp Arg Val Ala
1               5                   10                  15

Cys Phe Ala Cys Gly Gly Lys Leu Ser Asn Trp Glu Pro Lys Asp Asp
                20                  25                  30

Ala Met Ser Glu His Arg Arg His Phe Pro Asn Cys Pro Phe
            35                  40                  45
```

(2) INFORMATION FOR SEQ ID NO: 8:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

```
Leu Ala Lys Ala Gly Phe Tyr Tyr Ile Gly Pro Gly Asp Arg Val Ala
1               5                   10                  15

Cys Phe Ala Cys Gly Gly Lys Leu Ser Asn Trp Glu Pro Lys Asp Asn
                20                  25                  30

Ala Met Ser Glu His Leu Arg His Phe Pro Lys Cys Pro Phe
            35                  40                  45
```

(2) INFORMATION FOR SEQ ID NO: 9:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Pro Glu Gln Leu Ala Ser Ala Gly Phe Tyr Tyr Val Gly Arg Asn Asp
 1               5                  10                  15

Asp Val Lys Cys Phe Cys Cys Asp Gly Gly Leu Arg Cys Trp Glu Ser
            20                  25                  30

Gly Asp Asp Pro Trp Val Glu His Ala Lys Trp Phe Pro Arg Cys Glu
        35                  40                  45
```

(2) INFORMATION FOR SEQ ID NO: 10:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Pro Glu Gln Leu Ala Ser Ala Gly Phe Tyr Tyr Val Gly Asn Ser Asp
 1               5                  10                  15

Asp Val Lys Cys Phe Cys Cys Asp Gly Gly Leu Arg Cys Trp Glu Ser
            20                  25                  30

Gly Asp Asp Pro Trp Val Gln His Ala Lys Trp Phe Pro Arg Cys Glu
        35                  40                  45
```

(2) INFORMATION FOR SEQ ID NO: 11:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

```
Glu Glu Arg Thr Cys Lys Val Cys Met Asp Lys Glu Val Ser Val Val
 1               5                  10                  15

Phe Ile Pro Cys Gly His Leu Val Val Cys Gln Glu Cys Ala Pro Ser
            20                  25                  30

Leu Arg Lys Cys Pro Ile Cys Arg Gly Ile Ile Lys Gly Thr Val Arg
        35                  40                  45

Thr Phe Leu Ser
    50
```

(2) INFORMATION FOR SEQ ID NO: 12:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

```
Glu Glu Arg Thr Cys Lys Val Cys Met Asp Lys Glu Val Ser Ile Val
 1               5                  10                  15

Phe Ile Pro Cys Gly His Leu Val Cys Lys Asp Cys Ala Pro Ser
            20                  25                  30

Leu Arg Lys Cys Pro Ile Cys Arg Ser Thr Ile Lys Gly Thr Val Arg
        35                  40                  45
```

```
Thr Phe Leu Ser
   50
```

(2) INFORMATION FOR SEQ ID NO: 13:

(i) SEQUENCE CHARACTERISTICS:
        (A) LENGTH: 2862 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
TTCCTTTACA GTGAATACTG TAGTCTTAAT AGACCTGAGC TGACTGCTGC AGTTGATGTA      60
ACCCACTTTA GAGAATACTG TATGACATCT TCTCTAAGGA AAACCAGCTG CAGACTTCAC     120
TCAGTTCCTT TCATTTCATA GGAAAAGGAG TAGTTCAGAT GTCATGTTTA AGTCCTTATA     180
AGGGAAAAGA GCCTGAATAT ATGCCCTAGT ACCTAGGCTT CATAACTAGT AATAAGAAGT     240
TAGTTATGGG TAAATAGATC TCAGGTTACC CAGAAGAGTT CATGTGACCC CCAAAGAGTC     300
CTAACTAGTG TCTTGGCAAG TGAGACAGAT TTGTCCTGTG AGGGTGTCAA TTCACCAGTC     360
CAAGCAGAAG ACAATGAATC TATCCAGTCA GGTGTCTGTG GTGGAGATCT AGTGTCAAGT     420
GGTGAGAAAC TTCATCTGGA AGTTTAAGCG GTCAGAAATA CTATTACTAC TCATGGACAA     480
AACTGTCTCC CAGAGACTCG GCCAAGGTAC CTTACACCAA AAACTTAAAC GTATAATGGA     540
GAAGAGCACA ATCTTGTCAA ATTGGACAAA GGAGAGCGAA GAAAAAATGA AGTTTGACTT     600
TTCGTGTGAA CTCTACCGAA TGTCTACATA TTCAGCTTTT CCCAGGGGAG TTCCTGTCTC     660
AGAGAGGAGT CTGGCTCGTG CTGGCTTTTA TTATACAGGT GTGAATGACA AAGTCAAGTG     720
CTTCTGCTGT GGCCTGATGT TGGATAACTG GAAACAAGGG ACAGTCCTG TTGAAAAGCA      780
CAGACAGTTC TATCCCAGCT GCAGCTTTGT ACAGACTCTG CTTTCAGCCA GTCTGCAGTC     840
TCCATCTAAG AATATGTCTC CTGTGAAAAG TAGATTTGCA CATTCGTCAC CTCTGGAACG     900
AGGTGGCATT CACTCCAACC TGTGCTCTAG CCCTCTTAAT TCTAGAGCAG TGGAAGACTT     960
CTCATCAAGG ATGGATCCCT GCAGCTATGC CATGAGTACA GAAGAGGCCA GATTTCTTAC    1020
TTACAGTATG TGGCCTTTAA GTTTTCTGTC ACCAGCAGAG CTGGCCAGAG CTGGCTTCTA    1080
TTACATAGGG CCTGGAGACA GGGTGGCCTG TTTTGCCTGT GGTGGGAAAC TGAGCAACTG    1140
GGAACCAAAG GATGATGCTA TGTCAGAGCA CCGCAGACAT TTTCCCCACT GTCCATTTCT    1200
GGAAAATACT TCAGAAACAC AGAGGTTTAG TATATCAAAT CTAAGTATGC AGACACACTC    1260
TGCTCGATTG AGGACATTTC TGTACTGGCC ACCTAGTGTT CCTGTTCAGC CCGAGCAGCT    1320
TGCAAGTGCT GGATTCTATT ACGTGGATCG CAATGATGAT GTCAAGTGCT TTTGTTGTGA    1380
TGGTGGCTTG AGATGTTGGG AACCTGGAGA TGACCCCTGG ATAGAACACG CCAAATGGTT    1440
TCCAAGGTGT GAGTTCTTGA TACGGATGAA GGGTCAGGAG TTTGTTGATG AGATTCAAGC    1500
TAGATATCCT CATCTTCTTG AGCAGCTGTT GTCCACTTCA GACACCCCAG AGAAGAAAA    1560
TGCTGACCCT ACAGAGACAG TGGTGCATTT TGGCCCTGGA GAAAGTTCGG AAGATGTCGT    1620
CATGATGAGC ACGCCTGTGG TTAAAGCAGC CTTGGAAATG GGCTTCAGTA GGAGCCTGGT    1680
GAGACAGACG GTTCAGCGGC AGATCCTGGC CACTGGTGAG AACTACAGGA CCGTCAATGA    1740
TATTGTCTCA GTACTTTTGA ATGCTGAAGA TGAGAGAAGA GAAGAGGAGA AGGAAAGACA    1800
GACTGAAGAG ATGGCATCAG GTGACTTATC ACTGATTCGG AAGAATAGAA TGGCCCTCTT    1860
```

-continued

```
TCAACAGTTG ACACATGTCC TTCCTATCCT GGATAATCTT CTTGAGGCCA GTGTAATTAC    1920

AAAACAGGAA CATGATATTA TTAGACAGAA AACACAGATA CCCTTACAAG CAAGAGAGCT    1980

TATTGACACC GTTTTAGTCA AGGGAAATGC TGCAGCCAAC ATCTTCAAAA ACTCTCTGAA    2040

GGAAATTGAC TCCACGTTAT ATGAAAACTT ATTTGTGGAA AAGAATATGA AGTATATTCC    2100

AACAGAAGAC GTTTCAGGCT TGTCATTGGA AGAGCAGTTG CGGAGATTAC AAGAAGAACG    2160

AACTTGCAAA GTGTGTATGG ACAGAGAGGT TTCTATTGTG TTCATTCCGT GTGGTCATCT    2220

AGTAGTCTGC CAGGAATGTG CCCCTTCTCT AAGGAAGTGC CCCATCTGCA GGGGACAAT    2280

CAAGGGGACT GTGCGCACAT TTCTCTCATG AGTGAAGAAT GGTCTGAAAG TATTGTTGGA    2340

CATCAGAAGC TGTCAGAACA AAGAATGAAC TACTGATTTC AGCTCTTCAG CAGGACATTC    2400

TACTCTCTTT CAAGATTAGT AATCTTGCTT TATGAAGGGT AGCATTGTAT ATTTAAGCTT    2460

AGTCTGTTGC AAGGGAAGGT CTATGCTGTT GAGCTACAGG ACTGTGTCTG TTCCAGAGCA    2520

GGAGTTGGGA TGCTTGCTGT ATGTCCTTCA GGACTTCTTG GATTTGGAAT TTGTGAAAGC    2580

TTTGGATTCA GGTGATGTGG AGCTCAGAAA TCCTGAAACC AGTGGCTCTG GTACTCAGTA    2640

GTTAGGGTAC CCTGTGCTTC TTGGTGCTTT TCCTTTCTGG AAAATAAGGA TTTTTCTGCT    2700

ACTGGTAAAT ATTTTCTGTT TGTGAGAAAT ATATTAAAGT GTTTCTTTTA AAGGCGTGCA    2760

TCATTGTAGT GTGTGCAGGG ATGTATGCAG GCAAAACACT GTGTATATAA TAAATAAATC    2820

TTTTTAAAAA GTGAAAAAAA AAAAAAAAA AAAAAAAAA AA                        2862
```

(2) INFORMATION FOR SEQ ID NO: 14:

(i) SEQUENCE CHARACTERISTICS:
        (A) LENGTH: 612 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

```
Met Asp Lys Thr Val Ser Gln Arg Leu Gly Gln Gly Thr Leu His Gln
1               5                   10                  15

Lys Leu Lys Arg Ile Met Glu Lys Ser Thr Ile Leu Ser Asn Trp Thr
            20                  25                  30

Lys Ser Glu Glu Lys Met Lys Phe Asp Phe Ser Cys Glu Leu Tyr
        35                  40                  45

Arg Met Ser Thr Tyr Ser Ala Phe Pro Arg Gly Val Pro Val Ser Glu
    50                  55                  60

Arg Ser Leu Ala Arg Ala Gly Phe Tyr Tyr Thr Gly Val Asn Asp Lys
65                  70                  75                  80

Val Lys Cys Phe Cys Cys Gly Leu Met Leu Asp Asn Trp Lys Gln Gly
                85                  90                  95

Asp Ser Pro Val Glu Lys His Arg Gln Phe Tyr Pro Ser Cys Ser Phe
            100                 105                 110

Val Gln Thr Leu Leu Ser Ala Ser Leu Gln Ser Pro Ser Lys Asn Met
        115                 120                 125

Ser Pro Val Lys Ser Arg Phe Ala His Ser Ser Pro Leu Glu Arg Gly
    130                 135                 140

Gly Ile His Ser Asn Leu Cys Ser Ser Pro Leu Asn Ser Arg Ala Val
145                 150                 155                 160

Glu Asp Phe Ser Ser Arg Met Asp Pro Cys Ser Tyr Ala Met Ser Thr
                165                 170                 175
```

```
Glu Glu Ala Arg Phe Leu Thr Tyr Ser Met Trp Pro Leu Ser Phe Leu
            180                 185                 190

Ser Pro Ala Glu Leu Ala Arg Ala Gly Phe Tyr Tyr Ile Gly Pro Gly
            195                 200                 205

Asp Arg Val Ala Cys Phe Ala Cys Gly Gly Lys Leu Ser Asn Trp Glu
            210                 215                 220

Pro Lys Asp Asp Ala Met Ser Glu His Arg Arg His Phe Pro His Cys
225                 230                 235                 240

Pro Phe Leu Glu Asn Thr Ser Glu Thr Gln Arg Phe Ser Ile Ser Asn
                245                 250                 255

Leu Ser Met Gln Thr His Ser Ala Arg Leu Arg Thr Phe Leu Tyr Trp
            260                 265                 270

Pro Pro Ser Val Pro Val Gln Pro Glu Gln Leu Ala Ser Ala Gly Phe
            275                 280                 285

Tyr Tyr Val Asp Arg Asn Asp Asp Val Lys Cys Phe Cys Cys Asp Gly
            290                 295                 300

Gly Leu Arg Cys Trp Glu Pro Gly Asp Asp Pro Trp Ile Glu His Ala
305                 310                 315                 320

Lys Trp Phe Pro Arg Cys Glu Phe Leu Ile Arg Met Lys Gly Gln Glu
                325                 330                 335

Phe Val Asp Glu Ile Gln Ala Arg Tyr Pro His Leu Leu Glu Gln Leu
            340                 345                 350

Leu Ser Thr Ser Asp Thr Pro Gly Glu Glu Asn Ala Asp Pro Thr Glu
            355                 360                 365

Thr Val His Phe Gly Pro Gly Glu Ser Ser Glu Asp Val Val Met
            370                 375                 380

Met Ser Thr Pro Val Val Lys Ala Ala Leu Glu Met Gly Phe Ser Arg
385                 390                 395                 400

Ser Leu Val Arg Gln Thr Val Gln Arg Gln Ile Leu Ala Thr Gly Glu
                405                 410                 415

Asn Tyr Arg Thr Val Asn Asp Ile Val Ser Val Leu Leu Asn Ala Glu
            420                 425                 430

Asp Glu Arg Arg Glu Glu Lys Glu Arg Gln Thr Glu Glu Met Ala
            435                 440                 445

Ser Gly Asp Leu Ser Leu Ile Arg Lys Asn Arg Met Ala Leu Phe Gln
            450                 455                 460

Gln Leu Thr His Val Leu Pro Ile Leu Asp Asn Leu Leu Glu Ala Ser
465                 470                 475                 480

Val Ile Thr Lys Gln Glu His Asp Ile Ile Arg Gln Lys Thr Gln Ile
                485                 490                 495

Pro Leu Gln Ala Arg Glu Leu Ile Asp Thr Val Leu Val Lys Gly Asn
            500                 505                 510

Ala Ala Ala Asn Ile Phe Lys Asn Ser Leu Lys Glu Ile Asp Ser Thr
            515                 520                 525

Leu Tyr Glu Asn Leu Phe Val Glu Lys Asn Met Lys Tyr Ile Pro Thr
            530                 535                 540

Glu Asp Val Ser Gly Leu Ser Leu Glu Glu Gln Leu Arg Arg Leu Gln
545                 550                 555                 560

Glu Glu Arg Thr Cys Lys Val Cys Met Asp Arg Glu Val Ser Ile Val
                565                 570                 575

Phe Ile Pro Cys Gly His Leu Val Val Cys Gln Glu Cys Ala Pro Ser
            580                 585                 590
```

```
-continued

Leu Arg Lys Cys Pro Ile Cys Arg Gly Thr Ile Lys Gly Thr Val Arg
        595                 600                 605

Thr Phe Leu Ser
    610
```

INHIBITORS OF APOPTOSIS

CROSS-REFERENCE TO RELATED APPLICATION

This application is a Divisional of Ser. No. 09/689,366, filed Oct. 12, 2000, now U.S. Pat. No. 6,821,736 which is a Divisional of Ser. No. 08/569,749, filed Dec. 08, 1995, now U.S. Pat. No. 6,187,557, which is a continuation of Ser. No. 08/512,946, filed Aug. 08, 1995 now abandoned, all of which are incorporated herein by reference.

INTRODUCTION

1. Field of the Invention

The field of this invention is human proteins involved in the inhibition of apoptosis, or programmed cell death.

2. Background

Cellular apoptosis, or programmed cell death, may be initiated by a variety of different stimuli including viral infection, certain cell-culture conditions, cell-cell signaling, cytokines, etc. Elucidation of signal transduction pathways leading to apoptosis would provide valuable insight into a variety of pathogenic mechanisms. Accordingly, the ability to exogenously modulate the induction of apoptosis would yield therapeutic application for numerous clinical indications. In addition, components of such pathways would provide valuable targets for automated, cost-effective, high throughput drug screening and hence would have immediate application in domestic and international pharmaceutical and biotechnology drug development programs.

Relevant Literature

Rothe et al. (1994) Cell 78, 681–692, report the existence of tumor necrosis factor (TNF) receptor associated proteins which co-immunoprecipitate with a TNF receptor; see also Rothe, et al., pending U.S. patent application Ser. No: 08/446,915. Roy, et al. (1995) Cell 80, 167–178 disclose the gene for a human neuronal apoptosis inhibitory protein. Birnbaum et al. (1994) J Virol 68, 2521–2528 disclose an inhibitor of apoptosis (iap) gene, Op-iap from the Orgyia pseudotsugata nuclear polyhedrosis virus (OpMNPV) with sequence similarity to two other viral genes: Cp-iap derived from Cydia pomonella granulosis virus (CpGV), and iap derived from the Autographa califomica nuclear polyhedrosis virus (AcMNPV). Clem and Miller (1994), in Apoptosis II: The Molecular Basis of Apoptosis in Disease, pp 89–110, Cold Spring Harbor Laboratory Press, provide a recent review of apoptosis regulation by insect viruses.

SUMMARY OF THE INVENTION

The invention provides methods and compositions relating to novel human cellular inhibitor of apoptosis proteins (c-IAP). The subject proteins comprise a series of defined structural domain repeats and/or a RING finger domain; in particular, at least two of a first domain repeat comprising SEQUENCE ID NO: 5 or 6; a second domain repeat comprising SEQUENCE ID NO: 7 or 8; and a third domain repeat comprising SEQUENCE ID NO: 9 or 10; and/or a RING finger domain comprising SEQUENCE ID NO: 11 or 12, or a consensus sequences derived from these human genes. The proteins provide a c-IAP specific function, with preferred proteins being capable of modulating the induction of apoptosis; for example, by binding a human tumor necrosis factor receptor associated factor, TRAF. The compositions include nucleic acids which encode the subject c-IAP and hybridization probes and primers capable of hybridizing with the disclosed c-IAP genes.

The invention includes methods of using the subject compositions in therapy (e.g. gene therapy to enhance expression of a c-IAP gene), in diagnosis (e.g. genetic hybridization screens for c-IAP gene mutations, and in the biopharmaceutical industry (e.g. reagents for increasing yields of recombinant protein by enhancing host cell survival in culture, for screening chemical libraries for lead compounds for a pharmacological agent useful in the diagnosis or treatment of disease associated with apoptosis regulation, etc.).

DETAILED DESCRIPTION OF THE INVENTION

The invention provides methods and compositions relating to novel cellular inhibitor of apoptosis proteins (c-IAPs). The nucleotide sequence of a natural cDNA encoding human c-IAP is shown as SEQUENCE ID NO:1 and the full conceptual translate is shown as SEQUENCE ID NO:2. The nucleotide sequence of another natural cDNA encoding human c-IAP2 is shown as SEQUENCE ID NO:3 and the full conceptual translate is shown as SEQUENCE ID NO:4. The human c-IAPs of the invention include incomplete translates of SEQUENCE ID NOS:1 and 3 or deletion mutants of SEQUENCE ID NOS: 2 and/or 4, which translates or deletions mutants have at least one of the human c-IAP specific activities described herein. In addition, the invention provides nonhuman mammalian homologs of the disclosed human c-IAPs. These homologs are encoded by natural cDNAs which are capable of specifically hybridizing with one or more of the disclosed human cDNAs under hybridization conditions describe below and are isolated using the methods and reagents described herein. For example, the amino acid sequence of a murine homolog of c-IAP1, and the sequence its cDNA are shown in SEQUENCE ID NOS: 14 and 13.

The subject proteins comprise a series of defined structural domain repeats and/or a RING finger domain shown to be necessary for human c-IAP specific function; generally including at least two of: a first domain repeat comprising SEQUENCE ID NO: 5, 6 or a consensus of 5 and 6, a second domain repeat comprising SEQUENCE ID NO: 7, 8 or a consensus of 7 and 8, and a third domain repeat comprising SEQUENCE ID NO: 9, 10 or a consensus of 9 and 10; and/or a RING finger domain comprising SEQUENCE ID NO: 11, 12 or a consensus of 11 and 12. Preferred domain repeat containing c-IAPs contain each of the three domain repeats. More preferred c-IAPs comprise the three domain repeats and the C-terminal RING finger. To secure or optimize the requisite function for the protein, the repeats are usually preceded (N-terminally) and separated by intervening regions of about 10 to about 100 residues, which regions preferably derive from those found in the natural c-IAP1 and c-IAP2 translates. Similarly, the RING finger domain of RING finger domain containing c-IAPs containing proteins is usually preceded by an N-terminal region of about 10 to 300 residues, usually 100 to 300 residues, which region preferably derives from those found in the natural c-IAP1 and c-IAP2 translates.

The proteins provide a human c-IAP1 or c-IAP2 (c-IAP1/2 ) specific activity or function which may be determined by convenient in vitro, cell-based, or in vivo assays. Preferred proteins are capable of modulating the induction of apoptosis. Such activity or function may be demonstrated in cell culture (e.g. cell transfections) or in animals (e.g. in vivo gene therapy, transgenics). c-IAP1/2 specific function can also be demonstrated by specific binding to a c-IAP1/2 specific binding target, including natural binding targets and nonnatural targets such as c-IAP1/2 specific antibodies. For example, c-IAPs comprising at least two of SEQUENCE ID NOS: 6, 7 and 8 are capable of specifically binding human tumor necrosis factor receptor associated factors 1 and 2 (TRAF1 and TRAF2) in simple in vitro binding assays. Finally, specific function can be assayed immunologically by the ability of the subject protein to elicit a c-IAP1/2 specific antibody in a rodent or rabbit. Generally, human c-IAP1/2 -specificity of the binding agent is shown by binding equilibrium constants (usually at least about $10^7$ $M^{-1}$, preferably at least about $10^8$ $M^{-1}$, more preferably at least about $10^9$ $M^{-1}$). A wide variety of cell-based and cell-free assays may be used to demonstrate human c-IAP1/2 -specific binding; preferred are rapid in vitro, cell-free assays such as mediating or inhibiting human c-IAP1/2 -protein (e.g. human c-IAP1-TRAF2) binding, immunoassays, etc.

The claimed human c-IAP proteins are isolated, partially pure or pure and are typically recombinantly produced. An "isolated" protein for example, is unaccompanied by at least some of the material with which it is associated in its natural state and constitutes at least about 2%, and preferably at least about 5% by weight of the total protein in a given sample; a partially pure protein constitutes at least about 10%, preferably at least about 30%, and more preferably at least about 60% by weight of the total protein in a given sample; and a pure protein constitutes at least about 70%, preferably at least about 90%, and more preferably at least about 95% by weight of the total protein in a given sample. A wide variety of molecular and biochemical methods are available for generating and expressing the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

The invention provides human c-IAP1/2-specific binding agents including substrates, natural intracellular binding targets, etc. and methods of identifying and making such agents, and their use in diagnosis, therapy and pharmaceutical development. For example, human c-IAP1/2-specific agents are useful in a variety of diagnostic and therapeutic applications, especially where disease or disease prognosis is assoicated with improper utilization of a pathway involving human c-IAP1/2, e.g. apoptosis. Novel human c-IAP1/2-specific binding agents include human c-IAP1/2-specific antibodies and other natural intracellular binding agents identified with assays such as one- and two-hybrid screens, non-natural intracellular binding agents identified in screens of chemical libraries, etc.

The invention also provides nucleic acids encoding the subject proteins, which nucleic acids may be part of human c-IAP1/2-expression vectors and may be incorporated into recombinant cells for expression and screening, transgenic animals for functional studies (e.g. the efficacy of candidate drugs for disease associated with c-IAP1/2 mediated signal transduction), etc., and nucleic acid hybridization probes and replication/amplification primers having a human c-IAP1/2 cDNA specific sequence contained in SEQUENCE ID NO:1 or 3. Nucleic acids encoding human c-IAP1/2 are isolated from eukaryotic cells, preferably human cells, by screening cDNA libraries with probes or PCR primers derived from the disclosed human c-IAP1/2 cDNA.

In addition, the invention provides nucleic acids sharing sufficient sequence similarity with that of the disclosed human c-IAP1/2 cDNAs to effect hybridization thereto. Such human c-IAP1/2 cDNA homologs are capable of hybridizing to the human c-IAP1/2-encoding nucleic acid defined by SEQUENCE ID NO: 1 or 3 under stringency conditions characterized by a hybridization buffer comprising 30% formamide in 5×SSPE (0.18 M NaCl, 0.01 M $NaPO_4$, pH7.7, 0.001 M EDTA) buffer at a temperature of 42° C. and remaining bound when subject to washing at 42° C. with the 0.2×SSPE. Preferred nucleic acids will hybridize in a hybridization buffer comprising 50% formamide in 5×SSPE buffer at a temperature of 42° C. and remain bound when subject to washing at 42° C. with 0.2×SSPE buffer at 42° C. Human c-IAP1/2 cDNA homologs can also be characterized by BLASTX (Altschul et al. (1990) Basic Local Alignment Search Tool, J Mol Biol 215, 403–410) probability scores. Using this nucleic acid sequence search program BLASTX, complete coding region human c-IAP1/2 cDNA homologs provide a Probability P(N) score of less than 1.0e-200. More preferred nucleic acids encode c-IAPs with at least about 50%, preferably at least about 60%, more preferably at least 70% pair-wise identity to at least one of SEQUENCE ID NOS: 2 and 4.

The subject nucleic acids are isolated, i.e. constitute at least about 0.5%, preferably at least about 5% by weight of total nucleic acid present in a given fraction. The subject nucleic acids find a wide variety of applications including use as translatable transcripts, hybridization probes, PCR primers, therapeutic nucleic acids, etc.; use in detecting the presence of human c-IAP1/2 genes and gene transcripts, in detecting or amplifying nucleic acids encoding additional human c-IAP1/2 homologs and structural analogs, and in gene therapy applications. When used as expression constructs, the nucleic acids are usually recombinant, meaning they comprise a sequence joined to a nucleotide other than that which it is joined to on a natural chromosome. The subject nucleic acids may be contained within vectors, cells or organisms.

In diagnosis, c-IAP1/2 hybridization probes find use in identifying wild-type and mutant c-IAP1/2 alleles in clinical and laboratory samples. Mutant alleles are used to generate allele-specific oligonucleotide (ASO) probes for high-throughput clinical diagnoses. In therapy, therapeutic c-IAP1/2 nucleic acids are used to modulate cellular expression or intracellular concentration or availability of active c-IAP1/2. A wide variety of indications may be treated, either prophylactically or therapeutically with the subject compositions. For example, where cell-specific apoptosis or other limitation of cell growth is desired, e.g. neoproliferative disease, a reduction in c-IAP1/2 expression is effected by introducing into the targeted cell type c-IAP1/2 nucleic acids which reduce the functional expression of c-IAP1/2 gene products (e.g. nucleic acids capable of inhibiting translation of a c-IAP1/2 protein). Conditions for treatment include restenosis, where vascular smooth muscle cells are involved, inflammatory disease states, where endothelial cells, inflammatory cells and glomerular cells are involved, myocardial infarction, where heart muscle cells are involved, glomerular nephritis, where kidney cells are involved, transplant rejection where endothelial cells are involved, infectious diseases such as HIV infection where certain immune cells and other infected cells are involved, or the like.

These c-IAP1/2 inhibitory nucleic acids are typically antisense: single-stranded sequences comprising complements of the disclosed c-IAP1/2 encoding nucleic acid. Antisense modulation of the expression of a given c-IAP1/2 protein may employ c-IAP1/2 antisense nucleic acids operably linked to gene regulatory sequences. Cell are transfected with a vector comprising a c-IAP1/2 sequence with a promoter sequence oriented such that transcription of the gene yields an antisense transcript capable of binding to endogenous c-IAP1/2 protein encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a given c-IAP1/2 protein may be administered to the target cell, in or temporarily isolated from a host, at a concentration that results in a substantial reduction in expression of the targeted protein.

In other indications, e.g. certain hypersensitivities, atrophic diseases, etc., a reduction in apoptosis is desired. In these applications, an enhancement in c-IAP1/2 expression is effected by introducing into the targeted cell type c-IAP1/2 nucleic acids which increase the functional expression of c-IAP1/2 gene products. Conditions for treatment include multiple sclerosis, where certain neuronal cells are involved, inflammatory disease states such as rheumatoid arthritis, where bystander cells are involved, transplant rejection where graft cells are involved, infectious diseases such as HIV infection where certain uninfected host cells are involved, or the like. Such nucleic acids may be c-IAP1/2 expression vectors, vectors which upregulate the functional expression of an endogenous c-IAP1/2 allele, or replacement vectors for targeted correction of c-IAP1/2 mutant alleles.

Various techniques may be employed for introducing of the nucleic acids into viable cells. The techniques vary depending upon whether one is using the subject compositions in culture or in vivo in a host. Various techniques which have been found efficient include transfection with a retrovirus, viral coat protein-liposome mediated transfection, see Dzau et al., *Trends in Biotech* 11, 205–210 (1993). In some situations it is desirable to provide the nucleic acid source with an agent which targets the target cells, such as an antibody specific for a surface membrane protein on the target cell, a ligand for a receptor on the target cell, etc. Where liposomes are employed, proteins which bind to a surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. In liposomes, the nucleic acid concentration in the lumen will generally be in the range of about 0.01 $\mu$M to 10 $\mu$M. For other techniques, the concentration and application rate is determined empirically, using conventional techniques to determine desired ranges.

Application of the subject therapeutics may be systemic or local, i.e. administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way. Systemic administration of the nucleic acid may be effected using naked DNA, lipofection, liposomes with tissue targeting (e.g. antibody).

The invention provides methods and compositions for enhancing the yield of many recombinantly produced proteins, such as tissue plasminogen activator (t-PA), by increasing maximum cell densities and survival time of host production cells in culture. Specifically, cultured cells are transfected with nucleic acids which effect the up-regulation of endogenous c-IAP or the expression of an exogenous c-IAP. For example, nucleic acids encoding functional c-IAP operably linked to a transcriptional promoter are used to over-express the exogenous c-IAP in the host cell (see, experimental section, below). Such transformed cells demonstrate enhanced survival ability at elevated cell densities and over extended culture periods.

The invention provides efficient methods of identifying pharmacological agents or lead compounds for agents active at the level of a human c-IAP1/2 modulatable cellular function, particularly human c-IAP1/2 mediated signal transduction, especially in apoptosis. Generally, these screening methods involve assaying for compounds which modulate a human c-IAP1/2 interaction with a natural c-IAP1/2 binding target. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target indications may include infection, genetic disease, cell growth and regulatory disfunction, such as neoplasia, inflammation, hypersensitivity, etc.

A wide variety of assays for binding agents are provided including protein-protein binding assays, immunoassays, cell based assays, etc. The human c-IAP1/2 compositions used the methods are usually added in an isolated, partially pure or pure form and are typically recombinantly produced. The human c-IAP1/2 may be part of a fusion product with another peptide or polypeptide, e.g. a polypeptide that is capable of providing or enhancing protein-protein binding, stability under assay conditions (e.g. a tag for detection or anchoring), etc. The assay mixtures comprise a natural intracellular human c-IAP1/2 binding target such as a TRAF. While native binding targets may be used, it is frequently preferred to use portions (e.g. peptides, nucleic acid fragments) thereof so long as the portion provides binding affinity and avidity to the subject human c-IAP1/2 conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the human c-IAP1/2 specifically binds the cellular binding target, portion or analog with a reference binding affinity. The mixture components can be added in any order that provides for the requisite bindings. Incubations may be performed at any temperature which facilitates optimal binding, typically between 4 and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the agent-influenced binding between the human c-IAP1/2 and one or more binding targets is detected by any convenient way. For cell-free binding type assays, a separation step is often used to separate bound from unbound components. Separation may be effected by precipitation (e.g. TCA precipitation, immunoprecipitation, etc.), immobilization (e.g on a solid substrate), etc., followed by washing by, for examples, membrane filtration (e.g. Whatman's P-81 ion exchange paper, Polyfiltronic's hydrophobic GFC membrane, etc.), gel chromatography (e.g. gel filtration, affinity, etc.). In addition, one of the components usually comprises or is coupled to a label. A wide variety of labels may be employed-essentially any label that provides for detection of bound protein. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters.

The following experiments and examples are offered by way of illustration and not by way of limitation.

EXPERIMENTAL

The murine cellular inhibitor of apoptosis protein 1 (c-IAP1) was biochemically purified as a TNF-R2 associated protein using coimmunoprecipitation Rothe et al. (1994) supra. A large scale protein purification protocol provided material sufficient for peptide sequencing. Fully degenerate oligonucleotides corresponding to two of the isolated peptides were used to specifically amplify a 0.75 kb DNA fragment from mouse CT6 RNA by Reverse Transcription-PCR. This DNA fragment was used to isolate full-length cDNA clones from a mouse CT6 cDNA library by hybridization (50% formamide, 5×SSPE, 42° C.; filters washed at 42° C. with 0.2×SSPE, where 1×SSPE is 0.18 M NaCl, 0.01 M NaPO$_4$, pH7.7, 0.001 M EDTA).

DNA sequence analysis predicted an open reading frame encoding a 612 amino acid protein that shows significant sequence similarity (36% amino acid identity) with the 'inhibitor of apoptosis protein' (IAP) from insect viruses (Clem, R. J. and Miller, L. K., 1994, supra) and the human 'neuronal apoptosis inhibitory protein' (NAIP) (23% amino acid identity), that is involved in spinal muscular atrophy (SMA) an inherited disease in humans (Roy et., 1995, supra). To obtain the human c-IAP1 gene, the originally amplified mouse DNA fragment was used as a probe to screen a HeLa cDNA library (30% formamide, 5×SSPE, 42° C.; filters washed at 42° C. with 0.2×SSPE). Sequence analysis of the isolated cDNA clones revealed that they correspond to two distinct genes, designated c-IAP1 and c-IAP2. The human c-IAP1 cDNA encodes a protein of 618 amino acids that is 84% identical to murine c-IAP1. The human c-IAP2 cDNA encodes a protein of 604 amino acids that shares a high degree of amino acid identity with both murine and human c-IAP1 (72% and 73%, respectively) and represents another member of the IAP superfamily.

Comparison of the amino acid sequence of members of the IAP superfamily reveals that they are comprised of at least three distinct domains. The N-terminal region of all IAP family members is comprised of 'baculovirus IAP repeat' (BIR) motifs (Birnbaum et al., 1994, supra). While the viral proteins contain two repeats, the mammalian homologs (c-IAP1, -2) possess three BIR motifs. Similarly, NAIP contains three BIR repeats. In addition to BIR motifs viral IAPs contain a C-terminal RING finger motif. This Zn-binding domain is also present in c-IAP1 and -2 but not in NAIP. Thus c-IAP1 and -2 define a distinct subfamily within the IAP superfamily that contain three BIR motifs and a RING finger motif. A RING finger domain is also present at the N-terminus of TRAF2 and has been shown to be involved in TRAF2 signal transduction. The RING finger motifs of c-IAP1 and -2 share significant sequence homology with the RING finger domains of viral IAPs but no homology with the TRAF2 RING finger domain besides the conserved cysteine and histidine residues. The region between the BIR domain and the RING finger domain of c-IAP1 and -2 is strongly conserved but does not reveal any significant homology to other members of the IAP family or any other proteins in the NCBI database.

A yeast two-hybrid system was used to determine how c-IAP1 and -2 interact with TNF-R2 and/or TRAFs. The following results were obtained indistinguishably for c-IAP1 and c-IAP2. Two-hybrid analysis revealed that c-IAP1 does not directly interact with TNF-R2. However, a direct interaction could be detected between c-IAP1 and TRAF2. The conserved TRAF domain of TRAF2 (amino acids 264–501) is sufficient to mediate this interaction. Consistently, c-IAP1 also interacted with TRAF1. Further analysis demonstrated that the coiled-coil region within the TRAF domain of TRAF2 (amino acids 251–358) is required for interaction with c-IAP1. In contrast, the C-terminal region of the TRAF domain (amino acids 359–501) that mediates the association of TNF-R2 with TRAF2 is dispensable for interaction of c-IAP1 with TRAF2. Thus c-IAP1 and TNF-R2 bind to non-overlapping docking sites within the TRAF domain of TRAF2. Consistently, c-IAP1 does not interact with TRAF3 (e.g. Cheng et al. (1995), supra), which does not contain a coiled-coil region with sequence similarity to TRAF2/TRAF1. Deletion mutagenesis of c-IAP1 indicated that the N-terminal half of the protein containing the three BIR motifs (amino acids 1–336 of c-IAP1 and 1–396 of c-IAP2) is sufficient for interaction with TRAF2 and TRAF1. Similarly, combinations of two of the three BIR motifs e.g. amino acid residues 46–99 and 204–249 of c-IAP1 and 29–82 and 189–234 of c-IAP2, separated by IAP1 derived intervening sequences of varying lengths are assayed for TRAF1 and TRAF2 binding. This indicates that BIR motifs represent a novel protein:protein interaction domain. The RING finger domain of c-IAP1/2 (amino acids 571–618 of c-IAP1 and 557–604 of c-IAP2) is not required for interaction with TRAFs, but rather mediates subsequent steps in the c-IAP1/2 signaling cascade. Similarly, a variety of c-IAP1 derived N-terminal leader sequences fused to the c-IAP1 RING finger domain are used to assay signal transduction mediation. In an analogous situation, the RING finger domain of TRAF2 has been demonstrated to be required for TRAF2-mediated activation of NF-κKB.

A transfection based co-immunoprecipitation assay was used to investigate how c-IAP1 interacts with the complex of TNF-R2 and TRAFs. In this system c-IAP1 was N-terminally tagged with a FLAG epitope peptide and expressed in human embryonic 293 cells under the control of a constitutive CMV promotor (pRK vector). The c-IAP1 expression vector was transiently co-transfected into 293 cells with expression vectors for TNF-R2 and TRAFs. After 24–36 h, the cells were harvested and extracts immunoprecipitated with anti-TNF-R2 antibodies, followed by Western analysis with anti-FLAG antibodies. This assay demonstrated that while c-IAP1 associates directly with TRAF1 and TRAF2, its interaction with TNF-R2 is indirect and requires the heterocomplex of TRAF1 and TRAF2. Thus, c-IAP1 is a component of the TNF-R2 (CD40)/TRAF signaling complex.

To determine the functional properties of c-IAP1 transient transfection assays were performed in human rhabdomyosarcoma KYM1 cells. The results indicate that overexpression of c-IAP1 but not of control vector, TRAF1 or TRAF2 protects KYM1 cells from TNF-induced programmed cell death (apoptosis). Hence, c-IAP1 regulates the cellular response to TNF by modulating TNF responsiveness, e.g. the initiation of an apoptotic or protective program. The transient transfection assay also finds use as a drug screening assay. In this application, candidate agents are screened as above for their ability to modulate the ability of c-IAP1 to downregulate apoptosis.

EXAMPLES

1. Protocol for human c-IAP1-TRAF2 binding assay.

A. Reagents:

Neutralite Avidin: 20 µg/ml in PBS.

Blocking buffer: 5% BSA, 0.5% Tween 20 in PBS; 1 hour at room temperature.

Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.

$^{33}$P human c-IAP1 10×stock: $10^{-8}$–$10^{-6}$ M unlabeled human c-IAP1 supplemented with 200,000–250,000 cpm of labeled human c-IAP1/21 (Beckman counter). Place in the 4° C. microfridge during screening.

Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM NaVo$_3$ (Sigma # S-6508) in 10 ml of PBS.

TRAF2: $10^{-8}$–$10^{-5}$ M biotinylated truncated TRAF2 (residues 264–501) in PBS.

B. Preparation of assay plates:

Coat with 120 µl of stock N-Avidin per well overnight at 4° C.

Wash 2 times with 200 µl PBS.

Block with 150 µl of blocking buffer.

Wash 2 times with 200 µl PBS.

C. Assay:

Add 40 µl assay buffer/well.

Add 10 µl compound or extract.

Add 10 µl $^{33}$P-human c-IAP1 (20,000–25,000 cpm/0.1–10 pmoles/well=$10^{-9}$–$10^{-7}$ M final concentration).

Shake at 25° C. for 15 minutes.

Incubate additional 45 minutes at 25° C.

Add 40 µl biotinylated truncated TRAF2 (0.1–10 pmoles/40 µl in assay buffer)

Incubate 1 hour at room temperature.

Stop the reaction by washing 4 times with 200 µl PBS.

Add 150 µl scintillation cocktail.

Count in Topcount.

D. Controls for all assays (located on each plate):

a. Non-specific binding b. Soluble (non-biotinylated truncated TRAF2) at 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

| | | |
|---|---|---|
| SEQUENCE ID NO: 1, 2 | h (human) c-IAP1 | cDNA, protein |
| SEQUENCE ID NO: 3, 4 | h c-IAP2 | cDNA, protein |
| SEQUENCE ID NO: 5, 6 | h c-IAP1, 2 repeat 1 | protein, protein |
| SEQUENCE ID NO: 7, 8 | h c-IAP1, 2 repeat 2 | protein, protein |
| SEQUENCE ID NO: 9, 10 | h c-IAP1, 2 repeat 3 | protein, protein |
| SEQUENCE ID NO: 11, 12 | h c-IAP1, 2 RING finger | protein, protein |
| SEQUENCE ID NO: 13, 14 | m (murine) c-IAP | cDNA, protein |

What is claimed is:

1. A pharmaceutical composition comprising a polynucleotide which specifically hybridizes with SEQ ID NO:1 or 3, and inhibits cellular expression of c-IAP1 or c-IAP2 in vitro.

2. A composition according to claim 1, wherein the polynucleotide hybridizes with SEQ ID NO:1.

3. A composition according to claim 1, wherein the polynucleotide hybridizes with SEQ ID NO:3.

4. A composition according to claim 1, wherein the polynucleotide is single-stranded and antisense to SEQ ID NO:3.

5. A composition according to claim 1, wherein the polynucleotide is single-stranded and antisense to SEQ ID NO:3.

* * * * *